United States Patent [19]

Kishimoto et al.

[11] Patent Number: 5,204,345
[45] Date of Patent: Apr. 20, 1993

[54] 6-EPIFUMAGILLOLS AND THE PHARMACEUTICAL USE THEREOF

[75] Inventors: Shoji Kishimoto; Takeshi Fujita, both of Takarazuka, Japan

[73] Assignee: Takeda Chemical Industries, Ltd., Osaka, Japan

[21] Appl. No.: 489,010

[22] Filed: Mar. 6, 1990

[30] Foreign Application Priority Data

Mar. 6, 1989 [JP] Japan .................. 1-053536

[51] Int. Cl.$^5$ ................ A61K 31/535; A61K 31/335; C07D 413/14; C07D 303/02
[52] U.S. Cl. .................. 514/231.5; 514/255; 514/326; 514/343; 514/444; 514/475; 549/60; 549/332; 548/517; 546/226; 546/282; 544/147; 544/374
[58] Field of Search .................. 514/475, 231.5; 549/332; 544/147

[56] References Cited

FOREIGN PATENT DOCUMENTS 0354787  2/1990 European Pat. Off. .
0000476  1/1987 Japan .

OTHER PUBLICATIONS

Corey et al. "Total Synthesis of (±) Fumagillin" CA 76 153444s (1972).
Tarbell et al. II "The Chemistry of Fumagillin" CA 56 2401f (1962).
Belgian Patents Repnt. No. 42/69 col. 1 formula No. II-IV and #731495.
Chemical Patent Index, Basic Abstracts Journal Section B, Week 8706, Abstract No. 87-040948/06, Abstract of JP-A-476/1987.
J. A. DiPaolo, et al., Antibiotics Annual 1958-1959, pp. 541-546.
Journal of American Chem. Society, vol. 83, pp. 3096-3113 (1961).
The Journal of Antibiotics, vol. 41, pp. 999-1008 (1988).

*Primary Examiner*—C. Warren Ivy
*Assistant Examiner*—A. A. Owens
*Attorney, Agent, or Firm*—David G. Conlin; David S. Resnick; Gregory D. Williams

[57] ABSTRACT

The present invention relates to a compound of the formula:

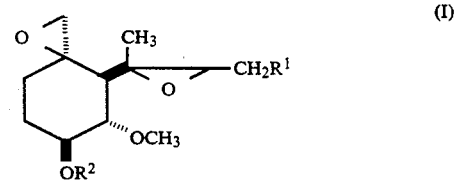

(I)

wherein $R^1$ is 2-methyl-1-propenyl group or isobutyl group; $R^2$ is hydrogen atom, an optionally substituted aliphatic hydrocarbon residue or an optionally substituted acyl group, or a salt thereof.

The compound (I) of the invention has, among others, angiogenesis inhibiting activity, cell-proliferation inhibiting activity and immune reaction inhibiting activity, thus being useful as medicines, etc.

8 Claims, No Drawings

6-EPIFUMAGILLOLS AND THE PHARMACEUTICAL USE THEREOF

TECHNICAL FIELD

The present invention relates to novel 6-epifumagillols or salts thereof, and production, and use thereof having activities of inhibiting, among others, angiogenesis, cell-proliferation and immune reactions, and having therapeutic and prophylactic activities against, for example, various inflammatory diseases (rheumatic diseases, psoriasis, etc.), diabetic retinopathy, arteriosclerosis, tumors and rejection symptoms in the case of internal organ transplantation.

BACKGROUND OF INVENTION

Angiogenesis is deeply concerned with occurrence or pathological processes of various inflammatory diseases (rheumatic diseases, psoriasis, etc.), diabetic retinopathy, tumors, etc. Therefore, it has been considered that inhibition of angiogenesis has a connection with therapy and prophylaxis of these diseases and several research groups have searched for substances capable of inhibiting angiogenesis. For example, mention is made of research works for application of Protamine by Taylor [Taylor, S. et al., Nature, 297, 307 (1982)] and for use of heparin in the presence of cortisone by Folkman et al. [Folkman, J. et al., Science, 221, 719 (1983)]. Furthermore, patent applications have been filed directed to ascorbic acid ether and its related compounds (JP-A-131978/1983) or polysaccharide sulfate DS4152 (JP-A-119500/1988) as compounds showing activity of inhibiting angiogenesis. However, the activities of these compounds are not sufficiently satisfactory, and compounds having more satisfactory activity desired.

Cell-proliferation is a function indispensable for growth and maintenance of living organisms. In higher animals, various tissues or organs have specific proliferation mechanisms which are controlled by various controlling substances. In recent years, numerous capable of substances positively controlling cell-proliferation, i.e., "cell-proliferation factors", have been isolated and purified. In addition, it has been made clear that these factors perform an important role in ontogeny and maintenance of life. On the other hand, there are many reports disclosing that abnormal cell-proliferation, especially when such proliferation is out of the control, is related with various diseases. Examples of such diseases include, tumors and arteriosclerosis.

Further, it has been discovered that various cell-proliferation factors participate in activation of immunocompetent cells, especially lymphocytes. Excess production or excess response of these cell-proliferation factors is considered to be one of the factors of aggravating autoimmune diseases or allergic diseases. Therefore, the use of medicines showing actions of selectively inhibiting cell-proliferation factors, controlling responses and of immunosuppression is considered to provide effective means of prophylaxis to cell-proliferation and therapy of these diseases, and also of suppressing graft rejection in internal organ transplantation.

OBJECT OF THE INVENTION

The object of the present invention lies in providing novel compounds having, among others, actions of inhibiting angiogenesis, suppressing cell-proliferation and immunosuppression.

For attaining the above-mentioned object, the present inventors have conducted searches for various compounds and evaluation of them. As a result, they found that 6-epifumagillol, chemically derived from fumagillin which has been known as an antibiotic agent and an antiprotozoal agent, and its related compounds have superb actions of inhibiting angiogenesis, suppressing cell-proliferation and immnosuppression, thus the present invention has been accomplished.

SUMMARY OF THE INVENTION

The present invention relates to 6-epifumagillols represented by the formula,

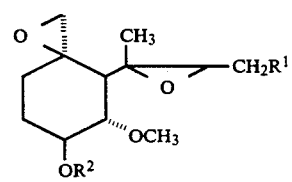

wherein $R^1$ stands for 2-methyl-1-propenyl group or isobutyl group; $R^2$ stands for hydrogen atom, an optionally substituted aliphatic hydrocarbon residue or an optionally substituted acyl group, and salts thereof.

DETAILED DESCRIPTION OF THE INVENTION

Examples of the aliphatic hydrocarbon residues of the optionally substituted aliphatic hydrocarbon residues shown by $R^2$ include straight-chained or branched alkyl groups, alkenyl groups, alkynyl groups or cycloaliphatic hydrocarbon residues, and, among others, alkyl groups are especially preferable.

Examples of the optionally substituted acyl groups shown by $R^2$ include acyl groups derived from carboxylic acid or its amide groups (e.g. alkanoyl group, aroyl group, aromatic heterocyclic carbonyl group, carbamoyl group, alkoxy carbonyl, phenoxy carbonyl group, etc.) or acyl groups derived from sulfonic acid or its amido groups, (e.g. benzenefulfonic group, sulfamoyl group, etc.).

Preferable embodiments of the above-mentioned $R^2$ are as follows. Examples of optionally substituted alkyl groups shown by $R^2$ include, $C_{1-20}$ straight-chain or branched alkyl groups optionally having 1-3 substituents. These alkyl groups may be epoxidated at optional positions. Among them, methyl, ethyl, benzyl, etc. are preferable. Examples of substituents of optionally substituted alkyl groups shown by $R^2$ include amino, lower alkyl amino (e.g. methylamino, ethylamino, isopropylamino, etc.), di-lower alkyl amino (e.g. diemthylamino, diethylamino, etc.), nitro, halogen (e.g. fluorine, chlorine, bromine, iodine, etc.), hydroxyl, lower alkoxy (e.g. methoxy, ethoxy, etc.), cyano, carbamoyl, carboxyl, lower alkoxycarbonyl (e.g. methoxycarbonyl, ethoxycarbonyl, etc.), carboxy lower alkoxy (carboxymethoxy, 2-carboxyethoxy, etc.), optionally substituted phenyl, aromatic heterocyclic groups (preferably 5-6 membered aromatic heterocyclic groups containing 1-4 hetero-atoms such as nitrogen, oxygen, sulfur, etc., such as 2-furyl, 2-thienyl, 4-thiazolyl, 4-imidazolyl, 4-pyridyl, etc.).

Examples of the optionally substituted alkanoyl groups shown by $R^2$ include alkanoyl groups optionally substituted with 1 to 3 substituents similar to those of the above-mentioned optionally substituted alkyl groups (preferably $C_{1-20}$ unsubstituted alkanoyl groups, e.g. formyl, acetyl, propionyl, isopropionyl, butyryl, pentanoyl, hexanoyl, heptanoyl, octanoyl, nonanoyl, lauroyl, undecanoyl, myristoyl, palmitoyl, stearoyl, arachinoyl, etc.). Among them, acetyl, butyryl, octanoyl, 3-carboxylpropionyl and 4-carboxybutyryl are preferable.

Examples of the optionally substituted aroyl groups shown by $R^2$ include benzoyl, 1-naphthoyl and 2-naphthoyl which may be substituted with $C_{2-6}$ lower alkyl such as ethyl, propyl etc., amino, halogen (e.g. fluorine, chlorine, bromine, etc.), hydroxyl, lower alkoxy (e.g. methoxy, ethoxy, etc.), cyano, carbamoyl, carboxyl, etc., preferably benzoyl optionally having 1 to 3 substituents, 1-naphthoyl, 2-naphthoyl, etc. Among them, benzoyl and 2-carboxybenzoyl are preferable.

Examples of the substituents in the optionally substituted aromatic heterocyclic carbonyl groups shown by $R^2$ include the same substituents as those of the above-mentioned substituted aroyl group. As the aromatic heterocyclic carbonyl groups, use is made of 5- or 6-membered ones containing 1 to 4 hetero atoms such as nitrogen, oxygen, sulfur, etc., and, among them, 2-furoyl, 2-thenoyl, nicotinoyl, isonicotinoyl, imidazole-1-carbonyl, etc. are preferable.

The optionally substituted carbamoyl groups shown by $R^2$ include carbamoyl group, mono-substituted carbamoyl group and di-substituted carbamoyl group, and substituents of them are exemplified by lower alkyl (e.g. methyl, ethyl, propyl, butyl, etc.) which may further be substituted by, for example, mono- or di-lower alkyl amino, lower alkanoyl (preferably $C_{1-6}$, e.g. formyl acetyl, propionyl, etc.), chloroacetyl, dichloroacetyl, trichloroacetyl, lower alkoxy carbonyl methyl (e.g. methoxy carbonyl methyl, ethoxy carbonyl methyl, etc.), carboxy methyl, optionally substituted phenyl, naphthyl, benzoyl, and substituents forming cyclic amino group (e.g. pyrrolidino, piperidino, morpholino, piperazino, 4-methylpiperazino, 4-phenylpiperazino, 4-ethyl-3,3-dioxopiperazino, etc.), taken together with the nitrogen atom of the carbamoyl group. Among them, chloroacetyl, phenyl and benzoyl are preferable.

As the optionally substituted alkoxycarbonyl groups shown by $R^2$, mention is made of, for example, straight-chain or branched lower alkoxycarbonyl groups which may have 1 to 3 substituents which are the same as those of the above-mentioned optionally substituted alkanoyl groups. Among them, are preferable methoxy carbonyl, ethoxy carbonyl, propoxy carbonyl, butoxy carbonyl, isobutoxy carbonyl and 1-chloroethoxy carbonyl.

Examples of substituents of the optionally substituted benzenesulfonyl group shown by $R^2$ include lower alkyl (e.g. methyl, ethyl, etc.), halogen (fluorine, chlorine, bromine, etc.), and one to three of these substituents may be located at optional positions of the benzene ring.

Examples of the substituents of optionally substituted phenoxycarbonyl groups shown by $R^2$ include the same substituents of the above-mentioned optionally substituted benzenesulfonyl groups, and one to three of these substituents may be substituted at optionally positions of phenoxy group.

Examples of optionally substituted alkylsulfonyl groups shown by $R^2$ include $C_{1-6}$ lower alkyl sulfonyl groups optionally having one to three of the same substituents as those of the above-mentioned optionally substituted alkanoyl groups. Among them, methyl sulfonyl and ethyl sulfonyl are preferable.

Examples of the optionally substituted sulfamoyl groups shown by $R^2$ include a lower alkyl (e.g. methyl, ethyl, propyl, isopropyl, isobutyl, etc.) and optionally substituted phenyl, and these substituents may be one or two which may be the same as or different from each other.

In the present specification, examples of substituents of optionally substituted phenyl groups include lower alkyl (e.g. methyl, ethyl, propyl, butyl, etc.), lower alkoxy (e.g. methoxy, ethoxy, propoxy, etc.), halogen (e.g. fluorine, chlorine, bromine, etc.), halogenated alkyl (e.g. trifluoromethyl, chloromethyl, etc.), nitro, etc., and one to five of these substituents may be substituted at optional positions of the phenyl ring.

And, in the present specification, unless otherwise specified, the lower alkyl group means $C_{1-6}$ straight-chain or branched alkyl groups, and the lower alkoxy group means $C_{1-6}$ alkoxy groups.

When the compound (I) of this invention has in its molecule an acidic substituent (e.g. carboxyl or the like) or a basic substituent (e.g. amino, lower alkylamino, di-lower alkylamino or the like), it can be used as a pharmacologically acceptable salt. As the pharmacologically acceptable salts, use is made of salts with inorganic bases, salts with organic bases, salts with basic or acid amino acid, or the like. As inorganic bases capable of forming these salts, use is made of, for example, an alkali metal (e.g. sodium, potassium, etc.), an alkaline earth metal (e.g. calcium, magnesium, etc.), etc.; as organic bases, use is made of trimethylamine, triethylamine, pyridine, picoline, N,N-dibenzylethylenediamine, ethanolamine, diethanolamine, tris-hydroxymethylaminomethane, dicyclohexylamine, etc.; as inorganic acids, use is made of, for example, hydrochloric acid, hydrobromic acid, sulfuric acid, nitric acid, phosphoric acid, etc.; as organic acids, use is made of, for example, formic acid, acetic acid, trifluoroacetic acid, oxalic acid, tartaric acid, fumaric acid, maleic acid, methanesulfonic acid, benzenesulfonic acid, p-toluenesulfonic acid, etc.; and. as basic or acid amino acids, use is made of, for example, arginine, lysine, ornithine, aspartic acid, glutamic acid, etc. Of these salts, those with bases (i.e. salts with inorganic bases, salts with organic bases, salts with basic amino acids) mean salts which can be formed with the carboxyl group in the substituents of compound (I), and, salts with acids (i.e. salts with inorganic acids, salts with organic acids, salts with acid amino acids) mean salts which can be formed with the amino group, lower alkylamino group, di-lower alkylamino group, etc. in the substituents of the compound (I).

A compound of the formula (I), wherein $R^1$ is 2-methyl-1-propenyl group, and $R^2$ is hydrogen atom, i.e. 6-epifumagillol is the compound derived from fumagillol which is the hydrolysate of fumagillin produced by a microorganism [Tarbell, D. S. et al., Journal of American Chemical Society, 83, 3096 (1961)] by subjecting to Mitsunobu reaction using diethyl azocarboxylate, triphenyl phosphine and a carboxylic acid such as formic acid or benzoic acid [Mitsunobu, O., Synthesis, 1981, p. 1], followed by hydrolysis.

Production of the compound (I), wherein $R^1$ is isobutyl group, $R^2$ is hydrogen atom, i.e. 6-epidihydrofumagillol can be accomplished by subjecting 6-epifumagillol to catalytic reduction under usual conditions (e.g. using 5% palladium-carbon in a methanol solution). This compound can also be obtained by subjecting fumagillol to catalytic reduction, followed by subjecting to Mitsunobu reaction and hydrolysis.

The compound (I), wherein $R^2$ is a substituent other than hydrogen atom, can be produced by subjecting 6-epifumagillol or 6-epidihydrofumagillol to alkylation or acylation (e.g. carbamoylation, sulfonylation) by, for example, the method described below, or by isolating the intermediates in those reactions. And, when $R^2$ is a group which does not change by catalytic reduction, 6-O-substituted-6-epifumagillol is subjected to catalytic reduction to convert into 6-O-substituted-6-epdihydrofumagillol. When the alkylating agent, acylating agent (carbamoylating agent, sulfonylating agent, etc.) have a substituent such as amino, hydroxyl, carboxyl etc., these substituents are preferably protected, and the protecting groups are selected in accordance with the stability of the product. Preferable examples of the protecting groups are, in the case of amino, 4-nitrobenzyloxycarbonyl, 2-trimethylsilylethoxycarbonyl, etc., and in case of hydroxyl, are 4-nitrobenzyl, t-butyl dimethylsilyl, etc., and, in case of carboxyl, are 4-nitrobenzyl, etc. For deprotection, a conventional means such as catalytic reduction or use of fluoride ion is employed. Additionally stating, in cases of carbamoylation and alkylation, it is possible that a lower alkyl such as methyl, ethyl, etc. is used as the protecting group of the carboxyl group, then, after the reaction, the protecting group is removed by hydrolysis under mild alkaline conditions.

1) Acylation by Carboxylic Acid

This acylation is conducted by allowing a reactive derivative of activated carboxylic acid such as acid anhydride or acid halide (acid chloride, acid bromide, etc.) to react with 6-epifumagillol or 6-epidihydrofumagillol (hereinafter referred to simply as starting alcohol).

Namely, the acylation is usually conducted by such reaction as shown by the following scheme:

Reactive derivative of $R^3OH$ + starting alcohol ⟶

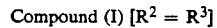

Compound (I) [$R^2 = R^3$]

(wherein $R^3$ stands for optionally substituted alkanoyl group, optionally substituted aroyl group and optionally substituted aromatic heterocyclic carbonyl group defined for $R^2$.)

Said reactive derivative of carboxylic acid is used usually in an amount of about 1 to 10 times mol., preferably 1 to 5 times mol., relative to 1 mol. of the starting alcohol.

This reaction is carried out usually in the presence of a base. Examples of the base include tertiary amine such as diisopropylethylamine, triethylamine, pyridine, N,N-dimethylaminopyridine, etc., alkali metal hydrogencarbonates such as sodium hydrogencarbonate, potassium hydrogencarbonate, etc., alkali metal carbonates such as potassium carbonate, sodium carbonate, etc., alkali metal hydride such as sodium hydride, potassium hydride, etc., organic metals such as butyl lithium, lithium diisopropylamide, etc., and the amount of the base to be added usually ranges from about 1 mol. to 10 times mol. relative to 1 mol. of the starting alcohol.

This reaction is conducted usually in an organic solvent which does not exert undesirable effects on the reaction. Examples of the organic solvent which does not exert undesirable effects on the reaction include amides such as dimethylformamide, dimethylacetamide, etc., halogenated hydrocarbons such as dichloromethane, chloroform, 1,2-dichloroethane, etc., ethers such as diethylether, tetrahydrofuran, dioxane, etc., esters such as methyl acetate, ethyl acetate, isobutyl acetate, methyl propionate, etc., nitriles such as acetonitrile, propionitrile, etc., nitro compounds such as nitromethane, nitroethane, etc., ketones such as acetone, methyl ethyl ketone, etc., aromatic hydrocarbons such as benzene, toluene, etc., and these may be used singly or as a mixture of two or more species in a suitable ratio. And, the tertiary amine employed as the base may be used as the solvent simultaneously.

The reaction temperature varies with the amounts, kinds, etc. of carboxylic derivatives, bases and solvents, and ranges from −80° C. to 100° C., preferably from 0° C. to room temperatures (in this specification, room temperatures represents a temperatures ranging from about 20° to about 35° C., unless otherwise specified). The reaction time ranges from about 30 minutes to about 5 days.

2) Alkylation

This alkylation is conducted by allowing a starting alcohol to react with an alkylating agent, for example, alkyl halide represented by the formula $R^4Y$ [wherein $R^4$ stands for, among the definition of $R^2$, an optionally substituted alkyl groups, and Y stands for a leaving group (e.g. halogen (chlorine, bromine, iodine, etc.))], dialkyl sulfate (e.g. methyl sulfate, diethyl sulfate, etc.). This alkylating agent is used in an amount of usually about 1 to 5 times mol. relative to the starting alcohol.

This reaction is conducted usually in the presence of a base. As the base, use is made of afore-mentioned alkali metal hydrogencarbonates, alkali metal carbonates, alkali metal hydrides, organic metals, etc., and the amount to be added ranges from about 1 to 5 times mol. relative to the starting alcohol.

This reaction is carried out usually in an organic solvent which does not exert undesirable influence on the reaction. Examples of such organic solvents as above include afore-mentioned amides, halogenated hydrocarbons, ethers, esters, nitriles, nitro-compounds, ketones and aromatic hydrocarbons, and these solvents can be used singly or as a mixture of two or more species of them in a suitable ratio.

The reaction temperature varies with the amounts, kinds etc., of alkylating agents, bases and solvents, and it ranges from −80 to 100 C, preferably from 0 C to room temperatures. The reaction time ranges from about 20 minutes to about 5 days.

3) Carbamoylation

Carbamoylation for introducing a mono-substituted carbamoyl group is carried out by usually allowing isocyanate to react with the starting amine, as, for example, shown by the following reaction scheme.

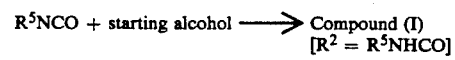

$R^5NCO$ + starting alcohol ⟶ Compound (I)
[$R^2 = R^5NHCO$]

(wherein $R^5$ stands for a substituent of the optionally substituted carbamoyl group shown by $R^2$ such as lower alkyl, lower alkanoyl chloroacetyl, etc.). The isocyanate is used in an amount of usually about 1 mol to 5 times mol. relative to 1 mol. of the starting alcohol.

This reaction is carried out usually in the presence of a base. As the base, use is made of above-mentioned tertiary amine, alkali metal hydrogencarbonates, alkali metal carbonates, alkali metal hydrides, organic metals, etc., and the amount of such a base as above to be added ranges from about 1 mol. to 5 times mol. relative to the starting alcohol.

This reaction is carried out usually in an organic solvent which does not exert undesirable influence on the reaction. Examples of such organic solvents as above include afore-mentioned amides, halogenated hydrocarbons, ethers, esters, nitriles, nitro-compounds, ketones and aromatic hydrocarbons, and these solvents can be used singly or as a mixture of two or more species of them in a suitable ratio. The tertiary amine employed as the base may be used as the solvent simultaneously.

The reaction temperature varies with the amounts and kinds of isocyanate, the base and the solvent then employed, and usually ranges from about $-80°$ C. to $100°$ C., preferably from $0°$ C. to room temperatures. The reaction time ranges from about one hour to about five days.

Among the compounds having mono-substituted carbamoyl group thus obtained, compounds having, for example, chloroacetylcarbamoyl, trichloroacetylcarbamoyl, etc., can be converted to compounds having carbamoyl group by removing chloroacetyl group or trichloroacetyl group by a conventional process (e.g. at room temperatures or an elevated temperatures under basic conditions).

The said carbamoylation can also be conducted by allowing the starting alcohol to react with carbamoyl halide.

The said carbamoyl halide is used in an amount of usually 1 mol. to 5 times mol. relative to 1 mol. of the starting alcohol.

This reaction is carried out usually in the presence of a base. As the base, use is made of the above-mentioned tertiary amine, alkali metal hydrogencarboantes, alkali metal carbonates, alkali metal hydrides, organic alkali metals, etc., and the amount of the base to be added ranges from about 1 mol. to 5 times mol. relative to the starting alcohol.

This reaction is carried out usually in an organic solvent which does not exert undesirable influence on the reaction. Examples of such organic solvents as above include afore-mentioned amides, halogenated hydrocarbons, ethers, esters, nitriles, nitro-compounds, ketones and aromatic hydrocarbons, and these solvents can be used singly or as a mixture of two or more species of them in a suitable ratio. The tertiary amine employed as the base may be used as the solvent simultaneously.

The reaction temperature varies with the amounts and kinds of carbamoyl halide, bases and solvents, and it ranges from about $0°$ C. to around reflux temperatures of the reaction medium, preferably from about $25°$ C. to reflux temperature.

The said carbamoylation can also be carried out by allowing the starting alcohol to react with chloroformic ester (e.g. phenyl chloroformate, ethyl chloroformate, isobutyl chloroformate, chloroformic acid 1-chloroethyl, etc.) or 1,1'-carbonyl diimidazole to give an active ester, followed by allowing the ester to react with primary or secondary amine. The said chloroformic esters or 1,1'-carbonyl diimidazole and amines are used in an amount usually ranging from 1 mol. to 5 times mol. relative to one mol. of the starting alcohol.

In this reaction, the reaction between the starting alcohol and chloroformic ester is carried out in the presence of a base. As the said base, use is made of the above-mentioned tertiary amine, alkali metal hydrogencarbonates, alkali metal carbonates, alkali metal hydrides, organic alkali metals, etc. The amount of the base to be added ranges usually from about 1 mol. to 5 times mol. relative to 1 mol. of the starting alcohol.

This reaction is carried out usually in an organic solvent which does not exert undesirable influence on the reaction. Examples of such organic solvents as above include afore-mentioned amides, halogenated hydrocarbons, ethers, esters, nitriles, nitro-compounds, ketones and aromatic hydrocarbons, and these solvents can be used singly or as a mixture of two or more species of them in a suitable ratio. The reaction temperature varies with the amounts and kinds of the chloroformic esters, bases, amines and solvents, and it ranges from $-20°$ C. to the reflux temperature of the reaction medium, preferably from $0°$ C. to $50°$ C. In addition, the active esters obtained as intermediates are also included in the compounds (I) which are the object compounds of the present application.

4) Sulfonylation

The sulfonylation is conducted by allowing an activated sulfonic acid derivative, for example, sulfonic anhydride, sulfonic halide (e.g. sulfonyl chloride, sulfonyl bromide, etc.) or sulfamoyl halide (e.g. sulfamoyl chloride, sulfamoyl bromide, etc.) to react with the starting alcohol.

More specifically, the reaction is performed as shown by the following scheme.

Reactive derivative of $R^6OH$ + starting alcohol $\longrightarrow$

Compound (I)
[$R^2 = R^6$]

[wherein $R^6$ stands for an optionally substituted benzene sulfonyl group, among the definition of $R^2$, or an optionally substituted alkyl sulfonyl group, or an optionally substituted sulfamoyl group].

The reactive derivative of the sulfonic acid is, generally, used in an amount of about 1 to 5 times mol. relative to 1 mol. of the starting alcohol.

This reaction is usually conducted in the presence of a base. As the base, use is made of the aforementioned tertiary amine, alkali metal hydrogencarbonates, alkali metal carbonates, alkali metal hydrides, organic metals, etc., and the amount thereof to be added is, generally, about 1 to 10 times mol. relative to 1 mol. of the starting alcohol.

This reaction is conducted usually in an organic solvent which does not exert an undesirable effect on the reaction. Examples of organic solvents exerting no undesirable effect on the reaction include the aforementioned amides, halogenated hydrocarbons, ethers, esters, nitriles, nitro compounds, ketones, and aromatic hydrocarbons, and these can be employed singly or as a mixture of two or more species of them in a suitable ratio. And, the tertiary amine employed as the base can be used also as the solvent.

The reaction temperature varies with amounts and kinds of the sulfonic acid or sulfamic acid derivatives, bases and solvents then employed, but it usually ranges from −80° C. to 100° C., preferably from 0° C. to room temperatures. The reaction time ranges from ten minutes to about 5 days.

Thus-produced 6-epifumagillol and related compounds (I) can be isolated by known separating and refining means (e.g. chromatography, crystallization), etc.

The compound (I) has an asymmetric center in the molecule and is thus possessed of optical activity, and its absolute structure is based on the starting fumagillol, which means that it is in agreement with the absolute structure of fumagillol.

The compounds of this invention show actions of, among others, inhibiting angiogenesis, cell-proliferation and immune reactions, and are useful as therapeutic and prophylactic agents of various inflammatory diseases (rheumatic diseases, psoriasis), diabetic retinopathy, arteriosclerosis, tumors and rejection symptoms in the case of internal organ transplantation. And, they can be safely administered orally or non-orally as they are or a pharmaceutical composition prepared by mixing with known pharmaceutically acceptable carriers, excipients, etc. [e.g. tablets, capsules (including soft capsules, microcapsules), liquids, injections, suppositories]. The dosage varies with, among others, subjects, routes and symptoms, but, usually, it ranges, in adults, from about 0.1 mg/kg to about 40 mg/kg body weight, preferably from about 0.5 mg/kg to about 20 mg/kg body weight per day.

EXPERIMENTAL EXAMPLE 1

The object compounds (I) obtained in the Examples given below were evaluated for angiogenesis inhibitory activity by the rat cornea micropocket method. The data obtained are summarized in Table 1. Method of Evaluation:

Essentially the same method of Gimbrone et al. [J. National Cancer Institute, 52, 413–419 (1974)] was followed. Thus, adult male Sprague-Dawley rats (11 to 16 week old) were anesthetized with nembutal and locally anesthetized by instillation of xylocaine eyedrops onto the eyeball. The cornea was incised to a length of about 2 mm at about 2 mm inside from the corneal circumference by means of an injection needle, and a basic fibroblast growth factor (bFGF; bovine brain-derived, purified product; R & D Inc.) and a sustained release pellet containing the test sample were inserted side by side into the incision so that the bFGF pellet was located on the central side in the cornea. In the control group, the bFGF pellet and a sample-free pellet were inserted into the cornea. After 10 days, the cornea was observed under a stereoscopic microscope. When the sample administration resulted in retardation or reduction of bFGF-induced angiogenesis, the sample was judged to have inhibitory activity.

The sustained release pellets were prepared in the following manner. An ethylene-vinyl acetate copolymer (Takeda Chemical Industries, Ltd.) was dissolved in dichloromethane to a concentration of 8%. A 3 μl portion of the solution was air-dried on a glass dish, an aqueous solution of bFGF (250 ng) was then placed thereon and air-dried and, finally 3 μl of the above ethylene-vinyl acetate copolymer solution was placed further thereon and air-dried to give a sandwich sheet. This sandwich sheet was made round into a bFGF pellet. The test sample pellets were prepared by dissolving each sample in ethanol in a concentration of 20 ug/2 μl, mixing the solution with 6 μl of an ethylene-vinyl acetate copolymer solution, air-drying the mixed solution in a glass dish and making the thus-obtained sheet round.

TABLE 1

| Angiogenesis inhibitory activity | | |
|---|---|---|
| Example No. | Inhibitory Rate | Judgment |
| 1 | 3/7 | ± |
| 2 | 3/7 | ± |
| 5 | 4/8 | ± |
| 6 | 6/6 | + |
| 7 | 5/6 | + |
| 8 | 5/7 | + |
| 12 | 3/4 | + |

In the Table 1 above, the inhibitory rate means the number of rats on which angiogenesis inhibitory activity was observed relative to the number of rats tested.

EXPERIMENTAL EXAMPLE 2

Evaluation of inhibition of human umbilical vein endothelial cell growth

Human umbilical vein endothelial cells were isolated by perfusion of an umbilical vein with a trypsin-containing medium. The cells were cultured in sequence in GIT medium (Daigo Eiyo Kagaku) supplemented with 2.5% fetal bovine serum and 2.0 ng/ml or recombinant human fibroblast growth factor (hereinafter simply referred to rFGF, prepared at Biotechnology Research Laboratories, Takeda Chemical Industries, Ltd.).

A suspension of human vein endothelial cells at the cell density of $2 \times 10^3$ (100 μl) was seeded on 96-well incubation plate (Nunc, 1-67008), and incubation was conducted in a gas-controlled thermostat vessel. The following day, 100 μl of medium containing rFGF (2 ng/ml at the final concentration) and samples of various concentrations were added. The samples were dissolved in dimethylsulfoxide (DMSO) and then diluted with culture medium so that the final DMSO concentration does not exceed 0.25%. After 5-day culture, the culture solution containing samples was removed by suction, 100 μl of 1 mg/ml of MTT solution [3-(4,5-dimethyl-2-thiazolyl)-2,5-diphenyl-2H-tetrazolium bromide was dissolved in the culture solution] was added and kept warm it about 40° C. for 4 hours. Then, 100 μl of a 10% SDS solution (aqueous solution of sodium dodecyl sulfate) was added, and the mixture was kept warming for 5–6 hours. The cells and MTT pigment were solubilized, and the $OD_{590}$ value was measured using a spectrophotometer. The OD value of the control group to which no test sample was added was set as 100%, and the activity of each test sample for inhibiting endothelial cell growth was shown in Table 2 by the concentration of the test compound giving 50% OD value, i.e. $IC_{50}$ value.

TABLE 2

| Activity of inhibiting endothelial cell growth | |
|---|---|
| Example No. | $IC_{50}$(ng/ml) |
| 1 | <0.08 |
| 2 | <0.08 |
| 3 | 9.82 |
| 5 | 1.91 |
| 6 | 2.05 |
| 7 | 8.71 |
| 8 | 0.166 |
| 9 | 0.1 |
| 11 | 4.68 |

TABLE 2-continued

Activity of inhibiting endothelial cell growth

| Example No. | IC$_{50}$(ng/ml) |
| --- | --- |
| 12 | 6.5 |

EXPERIMENTAL EXAMPLE 3

Immunosuppressive effects derivatives in vitro experiment

The effects of compound 5 (Example 5) and compound 8 (Example 8) on the $^3$H-thymidine uptake induced by the mixed lymphocyte reaction of spleen cells from BALB/c and C57BL/6 mice was examined. Compounds 5 and 8 showed 50% inhibition of $^3$H-thymidine uptake at concentrations of 0.3 and 0.01 μM, respectively.

The effects of compounds 5 and 8 on the antibody production induced by pokeweed mitogen, a T cell dependent B cell mitogen, and Epstein Barr virus, a T cell independent B cell mitogen, were examined. Compounds 5 and 8 showed 50% suppression of T cell dependent immunoglobulin production at concentrations of 7 and 4 μM, respectively. Also, compounds 5 and 8 showed 50% suppression of T cell independent antibody production at as low concentrations as 0.03 and 0.001 μM, respectively.

in vivo experiment

BALB/c mice were immunized with 50 μg of bovine gamma globulin mixed with Freund's complete adjuvant, and then 20 mg/kg of compounds 5 and 8, respectively, were intraperitoneally administered to the mice every 2 days after the immunization. Anti-bovine gamma globulin antibody titer was assayed in sera obtained 3 weeks after the immunization. The administration of compounds 5 and 8 induced significant suppression of anti-bovine gamma globulin antibody titer.

BALB/c mice were immunized with 10% sheep red blood cells, and then 100 mg/kg of compounds 5 and 8, respectively, were intraperitoneally administered to the mice once a day for 4 days after the immunization. The administrations of compounds 5 and 8 suppressed the formation of germinal center and the induction of plasma cells in the spleen on day 6 after the immunization. Such an obvious change was not observed in the cyclosporin A treated group.

Furthermore, the reduction of spleen weight was observed in the compounds 5 and 8 treated groups, but in the cyclosporin A treated group only the reduction of thymus weight was observed.

TABLE 3

| | Compound | | |
| --- | --- | --- | --- |
| Method | Compound 5 | Compound 8 | Cyclosporin A |
| in vitro[1]) | | | |
| Mixed lymphocyte reaction | 0.3 μM | 0.4 μM | 0.04 μM |
| T dependent Ab production | 7.0 μM | 4.0 μM | 0.004 μM |
| T independent Ab production | 0.03 μM | 0.001 μM | >10 μM |
| in vivo[2]) | | | |
| Anti-bovine gamma globulin Ab titer | 13% | 9% | 9% |
| Histological study in the spleen | | | |
| Inhibition of germinal center formation | + | + | − |
| Inhibition of plasma cell induction | + | + | − |
| Thymus weight | 105% | 116% | 46% |
| Spleen weight | 57% | 60% | 101% |

[1])The concentrations which showed 50% inhibitions were represented.
[2])Anti-bovine gamma globulin antibody titer and the weights of thymus and spleen were represented as percentages against those of a reference group which were injected with saline.

EXAMPLES

By the following examples, the present invention will be described in more detail, but the present invention is by no means limited to these examples.

The elution in the column chromatography in the following examples (bracketed terms are solvents used for elution) is conducted under observation by means of thin layer chromatography (TLC). In the TLC observation, as the TLC plate, Kieselgel 60F$_{250}$ (70 to 30 mesh, Merck) was employed, as the method of detection, a UV detector, a color-development method with phosphorus molybdate, etc. were employed. As the silica gel for the column, Kieselgel 60 (70 to 230 mesh, Merck) was employed. NMR spectrum shows proton NMR($^1$H-NMR), and, as interior or exterior standard, tetramethylsilane was employed, and the measurement was carried out by using Gemini 200 (VARIAN) showing the δ value in terms of ppm.

Abbreviations used in examples are as follows.

s: singlet, br: broad, d: doublet, dd: double doublet, ddd: doublet doublet doublet, t: triplet, q: quartet, m: multiplet, ABq: AB quartet, J: coupling constant, Hz: Hertz, CDCl$_3$: heavy chloroform, d$_6$-DMSO: heavy dimethyl sulfoxide, %: weight %

In the examples, "room temperatures" means temperatures ranging from about 15° to 25° C. Melting points and temperatures are all shown by centigrade.

EXAMPLE 1

Synthesis of 6-O-formyl-6-epifumagillol (1)

In tetrahydrofuran (100 ml) were dissolved fumagillol (4.0 g), triphenylphosphine (11.2 g) and formic acid (1.1 ml). To the solution was added dropwise a solution of diethyl azodicarboxylate (7.4 g) in tetrahydrofuran (20 ml). The mixture was stirred overnight, which was diluted with ethyl acetate (300 ml), followed by washing with a saturated aqueous solution of sodium chloride, then with a saturated aqueous solution of sodium hydrogencarbonate and further with a saturated aqueous solution of sodium hydrogencarbonate. The reaction mixture was dried over anhydrous magnesium sulfate, and the solvent was distilled off under reduced pressure. The residue was purified by means of silica gel chromatography (developing solvent: ethyl acetate - hexane=1:3) to afford 6-O-formyl-6-epifumagillol (2.6 g).

NMR spectrum (δ value; CDCl$_3$): 1.21(1H,m), 1.27(3H,s), 1.61(1H,d,11 Hz), 1.66(3H,s), 1.75(3H,s), 1.70 to 2.25(4H,m), 2.56(1H,m), 2.59(1H,d,4 Hz), 2.98(1H,d,4 Hz), 3.56(3H,s), 3.83(1H,dd,9 Hz,11 Hz), 5.00(1H,m), 5.20(1H,m), 8.17(1H,s).

EXAMPLE 2

Synthesis of 6-epifumagillol (2)

In methanol (20 ml) was dissolved the compound 1 (2.5 g), to which was added a conc. ammonia water (5 ml). The mixture was stirred for 15 minutes. The solvent was distilled under reduced pressure. The residue was dissolved in ethyl acetate (100 ml) and washed with a saturated aqueous solution of sodium chloride, which was dried over anhydrous magnesium sulfate. The solvent was then distilled off under reduced pressure. The residue was purified by means of silica gel chromatography (developing solvent: ethyl acetate - hexane=2:1) to afford 6-epifumagillol (1.8 g).

NMR spectrum ( $\delta$ value; CDCl$_3$): 1.22(1H,m), 1.30(3H,s), 1.54(1H,d,11Hz), 1.66(3H,s), 1.75(3H,s), 1.70 to 2.25(4H,m), 2.38(1H,m), 2.54(1H,d,4 Hz), 2.57(1H,t,7 Hz), 2.91(1H,d,4 Hz), 3.54 to 3.80(2H,m), 3.61(3H,s), 5.20(1H,m).

EXAMPLE 3

Synthesis of 6-O-methyl-6-epifumagillol (3)

In a mixture of tetrahydrofuran (1 ml) and dimethylformamide (1 ml) were dissolved the compound 2 (0.19 g) and methyl iodide (1 ml). To the solution was added under ice-cooling sodium hydride (0.2 g). The mixture was stirred for one hour at room temperature, to which was added water, followed by dilution with ether (30 ml). The solution was washed with water and a saturated aqueous solution of sodium chloride, which was dried over magnesium sulfate, followed by distilling off the solvent under reduced pressure. The residue was purified by means of silica gel chromatography (developing solvent: ethyl acetate - hexane=1:2) to afford 6-O-methyl-6-epifumagillol (0.18 g).

NMR spectrum ($\delta$ value; CDCl$_3$): 1.10(1H,m), 1.24(3H,s), 1.51(1H,d,11Hz), 1.66(3H,s), 1.74(3H,s), 1.5 to 2.45(5H,m), 2.54(2H,m), 2.93(1H,d,4 Hz), 3.28(1H,m), 3.48(3H,s), 3.58(1H,dd,9 Hz),11Hz), 3.64(3H,s), 5.21(1H,m).

EXAMPLE 4

Synthesis of 6-O-benzyl-6-epifumagillol (4)

In a mixture of tetrahydrofuran (1 ml) and dimethylformamide (1 ml) were dissolved the compound 2 (0.17 g) and benzyl bromide (0.16 g). To the solution was added sodium hydride (0.2 g) under ice-cooling. The mixture was stirred for 30 minutes, to which was added water, followed by dilution with ether (30 ml). The solution was washed with water and a saturated aqueous solution of sodium chloride, which was then dried over magnesium sulfate. The solvent was distilled off under reduced pressure. The residue was purified by means of silica gel chromatography (developing solvent: ethyl acetate - hexane=1:5) to afford 6-O-benzyl-6-epifumagillol (0.21 g).

NMR spectrum ($\delta$ value; CDCl$_3$): 1.08(1H,m), 1.25(3H,s), 1.51(1H,d,11Hz), 1.65(3H,s), 1.74(3H,s), 1.5 to 2.5(5H,m), 2.51(2H,m), 2.92(1H,d,4 Hz), 3.4 to 3.75(2H,m), 3.69(3H,s), 4.69(2H,s), 5.20(1H,m), 7.2 to 7.4(5H,m).

EXAMPLE 5

Synthesis of 6-O-acetyl-6-epifumagillol (5)

The compound 2 (0.20 g) was dissolved in dichloromethane (2 ml), to which were added acetic anhydride (0.13 ml) and dimethyl aminopyridine (10 mg). The mixture was stirred for 15 minutes, and then diluted with ethyl acetate (30 ml), followed by washing with a 1M aqueous solution of citric acid, a saturated aqueous solution of sodium chloride, a saturated aqueous solution of sodium hydrogencarbonate and further with a saturated aqueous solution of sodium chloride. The solution was dried over anhydrous magnesium sulfate. The solvent was distilled off under reduced pressure. The residue was purified by means of a silica gel chromatography (developing solvent: ethyl acetate - hexane=1:2) to afford 6-O-acetyl-6-epifumagillol (0.23 g).

NMR spectrum ($\delta$ value; CDCl$_3$): 1.19(1H,m), 1.26(3H,s), 1.60(1H,d,11Hz), 1.66(3H,s), 1.75(3H,s), 1.70 to 2.25(4H,m), 2.38(1H,m), 2.56(1H,t,7 Hz), 2.57(1H,d,4 Hz), 2.97(1H,d,4 Hz), 3.55(3H,s), 3.80(1H,dd,9 Hz,1Hz), 4.92(1H,m), 5.20(1H,m).

EXAMPLE 6

Synthesis of 6-O-benzoyl-6-epifumagillol (6)

In dichloromethane (2 ml) was dissolved the compound 2 (0.20 g) and dimethyl aminopyridine (0.13 g), to which was added dropwise at 0 C benzoyl chloride (0.1 ml). The mixture was stirred for 15 minutes at the same temperature, and then diluted with ethyl acetate (30 ml). The solution was washed with a saturated aqueous solution of sodium chloride, a 1M aqueous solution of citric acid and further with a saturated aqueous solution of sodium chloride. The resultant was dried over anhydrous magnesium sulfate, then the solvent was distilled off under reduced pressure. The residue was purified by means of silica gel chromatography (developing solvent: ethyl acetate - hexane=1:4) to afford 6-O-benzoyl-6-epifumagillol (0.26 g)

NMR spectrum ($\delta$ value; CDCl$_3$): 1.24(1H,m), 1.30(3H,s), 1.68(1H,d,1Hz), 1.68(3H,s), 1.75(3H,s), 1.70 to 2.25(4H,m), 2.38(1H,m), 2.59(1H,t,7 Hz), 2.60(1H,d,4 Hz), 3.01(1H,d,4 Hz), 3.59(3H,s), 3.97(1H,dd,9 Hz,11Hz), 5.10 to 5.28(2H,m), 7.42 to 7.64(3H,m), 8.10(2H,m).

EXAMPLE 7

Synthesis of 6-O-(3-carboxypropionyl)-6-epifumagillol (7)

In dichloromethane (1 ml) was dissolved the compound 2 (0.30 g) and dimethyl aminopyridine (0.39 g), to which was added succinic anhydride (0.21 g). The mixture was stirred for 15 minutes and then diluted with ethyl acetate (30 ml). The solution was washed with a 1M aqueous solution of citric acid, followed by washing three times with a saturated aqueous solution of sodium chloride. The resultant was dried over anhydrous magnesium sulfate. The solvent was distilled off under reduced pressure to afford 6-O-(3-carboxypropionyl)-6-epifumagillol (0.38 g).

NMR spectrum ($\delta$ value; CDCl$_3$): 1.19(1H,m), 1.26(3H,s), 1.61(1H,d,11Hz), 1.66(3H,s), 1.74(3H,s), 1.70 to 2.25(4H,m), 2.38(1H,m), 2.56(1H,t,8 Hz), 2.57(1H,d,4 Hz), 2.70(4H,m), 2.97(1H,d,4 Hz), 3.54(3H,s), 3.81(1H,dd,9 Hz,11Hz), 4.96(1H,m), 5.20(1H,m)

EXAMPLE 8

Synthesis of 6-O-phenoxycarbonyl-6-epifumagillol (8)

In dichloromethane (8 ml) were dissolved the compound 2 (0.53 g) and dimethyl aminopyridine (0.46 g). To the solution was added phenyl chloroformate (0.45 g), and then the mixture was stirred for 30 minutes. To the resultant was added water, and the mixture was diluted with dichloromethane (40 ml), followed by washing with water and a saturated aqueous solution of sodium chloride. The resultant was dried over magnesium sulfate, then the solvent was distilled off under reduced pressure. The residue was purified by means of a silica gel chromatography (developing solvent: ethyl acetate - hexane=1:5), which was then crystallized from ethanol to afford 6-O-phenoxycarbonyl-6-epifumagillol (0.55 g), m.p. 118° to 119° C.

NMR spectrum (δ value; CDCl$_3$): 1.22(1H,m), 1.28(3H,s), 1.63(1H,d,11Hz), 1.66(3H,s), 1.75(3H,s), 1.6 to 2.5(5H,m), 2.57(1H,t,7 Hz), 2.59(1H,d,4 Hz), 2.98(1H,d,4 Hz), 3.65(3H,s), 3.83(1H,d,4 Hz), 2.98(1H,d,4 Hz), 3.65(3H,s), 3.84(1H,dd,9 Hz,11Hz), 4.88(1H,m), 5.20(1H,m), 7.1 to 7.5(5H,m)

EXAMPLE 9

Synthesis of 6-O-carbamoyl-6-epifumagillol (9)

The compound 8 (0.16 g) was dissolved in ethanol (3 ml). To the solution was added a conc. aqueous ammonia (1 ml), and then the mixture was stirred for 3 hours at room temperature. The solvent was distilled off under reduced pressure. The residue was purified by means of silica gel chromatography (developing solvent: ethyl acetate - hexane=1:1) to afford 6-O-carbamoyl-6-epifumagillol (0.12 g), m.p. 52° to 53° C.

NMR spectrum (δ value; CDCl$_3$): 1.20(1H,m), 1.25(3H,s), 1.66(3H,s), 1.75(3H,s), 1.6 to 2.5(6H,m), 2.57(1H,t,7 Hz), 2.58(1H,d,4 Hz), 2.97(1H,d,4 Hz), 3.54(3H,s), 3.79(1H,dd,11Hz), 4.83(1H,m), 5.21(1H,m), 5.26(2H,brs).

EXAMPLE 10

Synthesis of 6-O-(N-chloroacetyl carbamoyl)-6-epifumagillol (10)

The compound 2 (0.30 g) was dissolved in dichloromethane (5 ml), to which was added dropwise at 0° C. chloroacetyl isocyanate (0.11 ml). The mixture was stirred for 15 minutes at the same temperature, which was diluted with ethyl acetate (50 ml), followed by washing with a saturated aqueous solution of sodium hydrogen carbonate, then with a saturated aqueous solution of sodium chloride. The resultant was dried over anhydrous magnesium sulfate, then the solvent was distilled off under reduced pressure. The residue was purified by means of a silica gel chromatography (developing solvent: ethyl acetate - hexane=1:3), followed by crystallization from isopropyl ether to afford 6-O-(N-chloroacetylcarbamoyl)-6-epifumagillol (0.25 g), m.p. 125° to 126° C.

NMR spectrum (δ value; CDCl$_3$): 1.24(1H,m), 1.26(3H,s), 1.66(3H,s), 1.75(3H,s), 1.70 to 2.25(5H,m), 2.38(1H,m), 2.56(1H,t,6 Hz), 2.61(1H,d,4 Hz), 2.99(1H,d,4 Hz), 3.55(3H,s), 3.83(1H,dd,9 Hz,11Hz), 4.52(2H,s), 4.92(1H,m), 5.20(1H,m), 8.06(1H,brs).

EXAMPLE 11

Synthesis of 6-O-morpholinocarbonyl-6-epifumagillol (11)

The compound 8 (0.17 g) was dissolved in dichloromethane (4 ml), to which was added morpholine (1 ml), and then the mixture was stirred for one day at room temperature. The reaction mixture was diluted with ethyl acetate (30 ml), which was washed with a saturated aqueous solution of ammonium chloride and a saturated aqueous solution of sodium chloride. The resultant was dried over magnesium sulfate, and the solvent was distilled off under reduced pressure. The residue was purified by means of a silica gel chromatography (developing solvent: ethyl acetate - hexane=1:2) to afford 6-O-morpholinocarbonyl-6-epifumagillol (0.13 g), m.p. 139° to 140° C.

NMR spectrum (δ value; CDCl$_3$): 1.20(1H,m), 1.26(3H,s), 1.66(3H,s), 1.75(3H,s), 1.6 to 2.6(7H,m), 2.58(1H,d,4 Hz), 2.97(1H,d,4 Hz), 3.50(4H,m), 3.54(3H,s), 3.67(4H,m), 3.80(1H,dd,9 Hz,11Hz), 4.87(1H,m), 5.21(1H,m).

EXAMPLE 12

Synthesis of 6-O-methanesulfonyl-6-epifumagillol (12)

The compound 2 (0.18 g) and dimethyl aminopyridine (0.15 g) were dissolved in dichloromethane (3 ml). To the solution was added dropwise, under ice-cooling, a solution of methanesulfonyl chloride (0.11 g) in dichloromethane (1 ml). The mixture was stirred for 30 minutes at room temperature, then the reaction mixture was diluted with ethyl acetate (30 ml), followed by washing with a saturated aqueous solution of ammonium chloride, water, then a saturated aqueous solution of sodium chloride. The resultant was dried over magnesium sulfate, then the solvent was distilled off under reduced pressure. The residue was purified by means of a silica gel chromatography (developing solvent: ethyl acetate - hexane=1:3) to afford 6-O-methanesulfonyl-6-epifumagillol (0.21 g).

NMR spectrum (δ value; CDCl$_3$): 1.29(3H,s), 1.56(1H,d,11Hz), 1.66(3H,s), 1.75(3H,s), 1.8 to 2.6(7H,m), 2.59(1H,d,4 Hz), 2.94(1H,d,4 Hz), 3.12(3H,s), 3.67(3H,s), 3.77(1H,dd,9 Hz,11Hz), 4.50(1H,m), 5.20(1H,m).

EXAMPLE 13

Synthesis of 6-O-(p-toluenesulfonyl)-6-epifumagillol (13)

The compound 2 (0.17 g) and dimethyl aminopyridine (0.15 g) were dissolved in dichloromethane (4 ml). To the solution was added p-toluenesulfonyl chloride (0.18 g). The mixture was then stirred for one day, which was diluted with ethyl acetate (30 ml), followed by washing with a saturated aqueous solution of ammonium chloride, water and a saturated aqueous solution of sodium chloride. The resultant was dried over magnesium sulfate, then the solvent was distilled off under reduced pressure. The residue was purified by means of a silica gel chromatography(developing solvent: ethyl acetate - hexane=1:3) to afford 6-O-(p-toluenesulfonyl)-6-epifumagillol (0.24 g).

NMR spectrum (δ value; CDCl$_3$): 1.20(1H,m), 1.21(3H,s), 1.47(1H,d,11Hz), 1.64(3H,s), 1.73((3H,s), 2.44(3H,s), 1.6 to 2.6(6H,m), 2.56(1H,d,4 Hz), 2.92(1H,d,4 Hz), 3.30(3H,s), 3.67(1H,dd,9 Hz),11Hz), 4.53(1H,m), 5.17(1H,m), 7.33(2H,d,8 Hz), 7.84(2H,d,8 Hz).

EXAMPLE 14

Synthesis of 6-epidihydrofumagillol (14)

A solution of the compound 2 (225 mg) in ethanol (7 ml) was subjected to catalytic reduction at normal pressure for 30 minutes at room temperature using 5% palladium carbon (200 mg) as the catalyst. The reaction mixture was subjected to filtration and the solvent was distilled off from the filtrate under reduced pressure. The residue was purified by means of silica gel chromatography (developing solvent: ethyl acetate - hexane=1:1) to afford 6-epidilydrofumagillol (0.17 g).

NMR spectrum (δ value: CDCl$_3$): 0.91(6H,d,J=6 Hz), 1.27(3H,s), 1.2 to 2.1(10H,m), 2.5 to 2.65(3H,m), 2.83(1H,d,J=4 Hz), 3.62(3H,s), 3.5 to 3.8(2H,m).

EXAMPLE 15

Synthesis of 6-O-(N-chloroacetylcarbamoyl)-6-epidihydrofumagillol (15)

In substantially the same manner as Example 10, 6-O-(N-chloroacetylcarbamoyl)-epidihydrofumagillol (0.18 g) was obtained from the compound 15 (0.16 g) and chloroacetyl isocyanate (0.11 g).

NMR spectrum (δ value; CDCl$_3$): 0.91(6H,d,J=7Hz), 1.23(3H,s), 1.2 to 2.2(10H,m), 2.53(1H,dd,J=7 Hz, J=5 Hz), 2.90(1H,d,J=4 Hz), 3.25(3H,s), 3.82(1H,dd,J=11Hz,9 Hz), 4.52(2H,s), 4.95(1H,m), 8.14(1H,brs).

EXAMPLE 16

Synthesis of 6-O-(2-dimethylaminoethylcarbamoyl)-6-epifumagillol (16)

To a solution of compound 8 (1.17 g) in dichloromethane (8 ml), was added dimethylaminoethylamine (1.1 g) and stirred over night at room temperature. The reaction mixture was concentrated under reduced pressure, and the residue was purified by means of silica gel column chromatography (developing solvent: dichloromethane-methanol-concentrated ammonia water=10:1:0.01) to obtain 6-O-(2-dimethylaminoethylcarbamoyl)-6-epifumagillol (0.71 g).

NMR spectrum (δ value, CDCl$_3$): 1.10(1H,m), 1.26(3H,s), 1.66(3H,s), 1.75(3H,s), 2.24 (6H,s), 1.5–2.5(8H,m), 2.55(1H,t,6 Hz), 2.56(1H,d,4 Hz), 2.96(1H,d,4 Hz), 3.29(2H,m), 3.52(3H,s), 3.78(1H,dd,11Hz,9 Hz), 4.87(1H,m), 5.15–5.3(2H,m).

EXAMPLE 17

Synthesis of 6-O-(2,4-difluorophenylcarbamoyl)-6-epifumagillol (17)

To a solution of compound 2 (1 g) and dimethylaminopyridine (0.2 g) in dichloromethane (7 ml), was added 2,4-difluorophenylisocyanate (1.37 g) and stirred at room temperature for 30 minutes. The reaction mixture was diluted by ethyl acetate (100 ml) and washed with an aqueous 1M citric acid, an aqueous saturated sodium hydrogencarbonate and an aqueous saturated sodium chloride. The resultant was dried over anhydrous magnesium sulfate, then the solvent was distilled off under reduced pressure.

The resulting residue was purified by means of silica gel column chromatography (developing solvent: ethyl acetate-hexane=4:1) to obtain 6-O-(2,4-difluorophenylcarbamoyl)-6-epifumagillol (1.15 g).

NMR spectrum (δ value, CDCl$_3$): 1.21(1H,m), 1.28(3H,s), 1.64(1H,d,11Hz), 1.67(3H,s), 1.75(3H,s), 1.7–2.5(5H,m), 2.57(1H,t,7 Hz), 2.59(1H,d,4 Hz), 2.99 (1H,d,4 Hz), 3.55(3H,s), 3.85(1H,dd,11Hz,9 Hz), 4.97(1H,m), 5.22(1H,m), 6.78(1H,brs), 6.8–6.95(2H,m),8.03(1H,m).

EXAMPLE 18

Synthesis of 6-O-[1-(4-ethyl-2,3-dioxopiperazinyl)carbamoyl]-6-epifumagillol (18)

To a solution of compound 2 (1.28 g) and dimethylaminopyridine (1.11 g) in dichloromethane (8 ml), was added 1-(4-ethyl-2,3-dioxopiperazinyl)carbonyl chloride (1.20 g) and stirred at room temperature for 15 minutes. The reaction mixture was dilluted with ethyl acetate (100 ml) and washed with an aqueous solution of saturated sodium hydrogencarbonate, water and a aqueous solution of saturated sodium chloride. The resultant was dried over anhydrous magnesium sulfate, then the solvent was distilled off under reduced pressure. The resulting residue was purified by means of silica gel column chromatogaphy (developing solvent: ethyl acetate-hesane=1:1) to obtain 6-O-[1-(4-ethyl-2,3-dioxopiperazinyl)carbamoyl]-6-epifumagillol (0.24 g). m.p.: 161°–162° C.

NMR spectrum (δ value, CDCl$_3$): 1.20(1H,m), 1.23(3H,t,7 Hz), 1.27(3H,s), 1.60(1H,d,11Hz), 1.66(3H,s), 1.75(3H,s), 1.6–2.5(5H,m), 2.56(1H,t,7 Hz), 2.58(1H,d,4 Hz), 2.97(1H,d,4 Hz), 3.5–3.7(4H,m), 3.63(3H,s), 3.91(1H,dd,11Hz,9 Hz), 4.09(2H,m), 4.95(1H,m), 5.21(1H,m).

What is claimed is:

1. A compound of the formula:

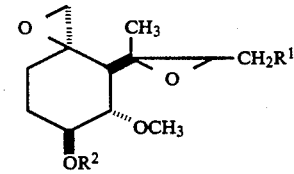

wherein R$^1$ is 2-methyl-1-propenyl group or isobutyl group; R$^2$ is (1) hydrogen atom;
(2) a C$_{1-20}$ alkanoyl which may be substituted with an amino, hydroxyl, halogen or carboxyl;
(3) a benzoyl or naphthoyl which may be substituted with a C$_{2-6}$ alkyl, amino, halogen, hydroxyl, C$_{1-6}$ alkoxy, cyano, carbamoyl or carboxyl;
(4) a 2-furoyl, 2-thienoyl, nicotinoyl, isonicotinoyl, or imidazole-1-carbonyl group which may be substituted with a C$_{2-6}$ alkyl, amino, halogen, hydroxyl, C$_{1-6}$ alkoxy, cyano, carbamoyl or carboxyl;
(5) a carbamoyl which may be substituted with a C$_{1-6}$ alkyl, C$_{1-6}$ alkanoyl, chloroacetyl, dichloroacetyl, trichloroacetyl, C$_{1-6}$ alkoxycarbonylmethyl, carboxymethyl, phenyl, naphthyl or benzoyl, or form a cyclic amino group together with the adjacent nitrogen atom selected from the group consisting of pyrrolidino, piperidino, morpholino, piperazino or 4-phenylpiperazino;
(6) a C$_{1-6}$ alkoxycarbonyl which may be substituted with an amino, hydroxyl, halogen or carboxyl;
(7) a phenoxycarbonyl which may be substituted with a C$_{1-6}$ alkyl or halogen;
(8) a benzenesulfonyl which may be substituted with one to three substituents selected from a C$_{1-6}$ alkyl and halogen;
(9) a C$_{1-6}$ alkylsulfonyl which may be substituted with an amino, hydroxyl, halogen or carboxyl; or

(10) a sulfamoyl which may be substituted with a C$_{1-6}$ alkyl or phenyl, or a salt thereof.

2. The compound as claimed in claim 1, wherein R$^1$ is 2-methyl-1-propenyl group.

3. The compound as claimed in claim 1, wherein R$^2$ is hydrogen atom.

4. The compound as claimed in claim 1, wherein R$^1$ is 2-methyl-1-propenyl group and R$^2$ is hydrogen, C$_{1-6}$ alkanoyl or phenoxycarbonyl.

5. The compound as claimed in claim 1, which is 6-epifumagillol.

6. The compound as claimed in claim 1, which is 6-O-acetyl-6-epifumagillol.

7. The compound as claimed in claim 1, which is 6-O-phenoxycarbonyl-6-epifumagillol.

8. A pharmaceutical composition for inhibiting immune reactions which comprises an effective amount of the compound as claimed in claim 1 and a pharmaceutically acceptable carrier, diluent or excipient.

* * * * *